United States Patent [19]

Cho

[11] Patent Number: 4,599,514

[45] Date of Patent: Jul. 8, 1986

[54] ISOTOPIC RADIATION METHOD AND APPARATUS FOR MEASURING THE RESINOUS BINDER APPLIED TO A MAT OF GLASS FIBERS

[75] Inventor: Boong Y. Cho, Columbus, Ohio

[73] Assignee: AccuRay Corporation, Columbus, Ohio

[21] Appl. No.: 449,276

[22] Filed: Dec. 13, 1982

[51] Int. Cl.[4] .............................................. G01F 23/00
[52] U.S. Cl. .................................... 250/359.1; 378/53
[58] Field of Search .................. 250/339, 358.1, 359.1, 250/360.1; 378/53

[56] References Cited

U.S. PATENT DOCUMENTS 3,087,061  4/1963  Dukes et al. .
3,092,724  6/1963  Foster .
3,417,244  12/1968  Kramer .
3,525,863  8/1970  Constantine .
3,626,183  12/1971  Berry .
3,809,903  5/1974  Cho .
3,889,121  6/1975  Bossen .............................. 250/359.1
4,037,104  7/1977  Allport .
4,090,074  5/1978  Watt .
4,363,968  12/1982  McGowan et al. .................. 250/339

Primary Examiner—Janice A. Howell
Attorney, Agent, or Firm—C. Henry Peterson

[57] ABSTRACT

A traveling mat (10) of glass fibers that have been coated with a resinous binder is measured so as to determine quantitatively the mass of binder per unit area of the mat, by directing into the traveling mat gamma rays (26) from a first radiation source (28) comprising americium-241 isotope, also directing into the traveling mat isotopic X-rays (30) from a second radiation source (32) comprising curium-244 isotope, detecting (at 22) the gamma rays from the traveling mat to produce a first response ($R_A$), detecting (at 24) the isotopic X-rays from the traveling mat to produce a second response ($R_C$) and forming (at 48) a combination of the first and second responses so as to produce a third response (B) that is indicative of the mass of the binder and substantially independent of the mass of the glass fibers.

8 Claims, 2 Drawing Figures

ISOTOPIC RADIATION METHOD AND APPARATUS FOR MEASURING THE RESINOUS BINDER APPLIED TO A MAT OF GLASS FIBERS

RELATED APPLICATIONS

Reference can be made to my copending application Ser. No. 302,959, filed Sept. 17, 1981 for MEASURING SYSTEM, and to the copending application of Steven P. Sturm, Ser. No. 431,179, filed Sept. 30, 1982 for MEASURING AND CONTROLLING METHODS AND APPARATUS. These applications are commonly assigned, and the disclosures of both applications are incorporated herein by reference.

TECHNICAL FIELD

This invention relates to a method and apparatus for measuring a traveling mat of glass fibers that have been coated with a resinous binder, so as to determine quantitatively the mass of binder per unit area of the mat. More particularly the invention relates to such a method and apparatus wherein one reponse is obtained using gamma radiation from the americium-241 isotope, and another response is obtained using isotopic X-rays from the curium-244 isotope. Combination of these responses provides a third response that is indicative of the mass of the binder and substantially independent of the mass of the glass fibers. If desired, another combination provides a fourth response that is indicative of the mass of the glass fibers and substantially independent of the mass of the binder.

BACKGROUND ART

In the manufacture of glass fiber mats, typically glass fiber is spun from molten glass and is sprayed with uncured binder compound as the fiber is being showered onto a moving chain conveyor. The conveyor carries the resulting glass fiber blanket through curing ovens wherein the binder material is exposed to elevated temperatures for an appropriate time period to complete the curing of the binder. After its exit from the ovens, the mat or blanket is cooled by a stream of air from a fan, and certain of its properties may be measured, typically with radiation gauges.

The mass per unit area of the traveling mat has been measured, with various degrees of success, using beta ray gauges, gamma ray or X-ray gauges, or infrared radiation gauges using combinations of wavelengths. One special example disclosed in our U.S. Pat. No. 3,809,903 uses gamma rays from the americium-241 isotope to generate substantially monochromatic X-rays in the range of about 14 to 30 kev, which in turn are used in the mass per unit area measurement. Very recently, curium-244 sources have become available, and commercially successful gauges for glass fiber mats have made use of the substantially monochromatic X-rays, in the range of about 14 to 21 kev, from this isotope as such for the mass per unit area measurements. The mass per unit area measurements have been used to automatically control the speed of the chain conveyor, thereby determining the amount of coated glass fibers deposited while a section of the conveyor moves through the felting chamber, with the objective of maintaining the weight per unit area of the mat constant along its length.

Various attempts have been made to measure the mass of the binder material per se, for example by taking advantage of the fact that glass is substantially transparent to certain optical (e.g., infrared) and X-ray wavelengths that are more or less attenuated by the binder materials. The objective of this measurement is to be able to control the mass of the binder by regulating the amount or the dilution of the spray material applied.

In the Sturm application No. 431,179 supra, it is proposed to measure the degree of cure of the resinous binder which has been effected by its exposure to the elevated temperatures in the curing ovens, and to automatically control the oven temperatures in response to the cure measurement. The cure measurement utilizes infrared radiation absorption, which is influenced somewhat by scattering effects in the thick glass fiber mat and by the spectral effects of certain constituents such as iron oxide that are accidentally present in variable unknown amounts in the glass from which the fibers are spun. These extraneous scattering and spectral effects on the infrared measurements are compensated by the use of a mass per unit area signal derived independently from a gamma ray or isotopic X-ray gauge. The computation of cure involves a set of variable values representing the mass per unit area of the binder material per se in the glass fiber mat, which values are obtained basically from the infrared absorption measurements. However, in the case of very heavy glass fiber mats (large mass per unit area) the infrared radiation has insufficient penetrating power to provide the binder mass information.

Hence there has been a need for an improved instrument capable of measuring quantitatively and reliably the mass of resinous binder per unit area of heavy glass fiber mats, which may be of the kind referred to as high-density mats and are used, for example, as heat insulation for refrigerator doors or as sound-deadening and heat-insulating mats under automobile hoods. Such mats typically range in thickness from about one-half to five inches (1.3 to 13 centimeters) and in mass per unit area from about 3000–8000 grams per square meter, of which about six to fourteen percent is binder, made up of cured components of urea formaldehyde and phenol formaldehyde. The "binder weight" measurement is difficult because of the macrostructure and microstructure of the mat and by the relatively small amount of binder as compared to the weight of the glass fibers. Moreover, while the effective atomic numbers of the glass and the binder are sufficiently different to provide a workable contrast for the purposes of more ordinary X-ray or gamma-ray measurements, they are not markedly different.

DISCLOSURE OF INVENTION

In accordance with this invention, there is provided a method of, and apparatus for measuring a traveling mat of glass fibers that have been coated with a resinous binder, so as to determine quantitatively the mass of binder per unit area of the mat, comprising method steps and elements of apparatus for directing into the traveling mat gamma rays from a first radiation source comprising americium-241 isotope, also directing into the traveling mat isotopic X-rays from a second radiation source comprising curium-244 isotope, detecting the gamma rays from the traveling mat to produce a first response, detecting the isotopic X-rays from the traveling mat to produce a second response, and forming a combination of the first and second responses so as to produce a third response that is indicative of the mass of the binder and substantially independent of the mass of the glass fibers.

Typically the first and second responses are calibrated so that both responses are adapted to correctly indicate the mass per unit area of a mat of glass fibers having no resinous binder thereon, and the combination is formed from the calibrated responses. A second combination of the first and second responses may be formed so as to produce a fourth response that is indicative of the mass of the glass fibers and substantially independent of the mass of the binder.

The object of this invention is to provide a highly stable, reasonably accurate and relatively inexpensive method and apparatus for measuring the binder mass per unit area in heavy glass fiber mats.

Further objects and advantages of the invention will become apparent from the following detailed description, taken in conjunction with the appended drawings.

BEST MODE FOR CARRYING OUT THE INVENTION

Figure 1:
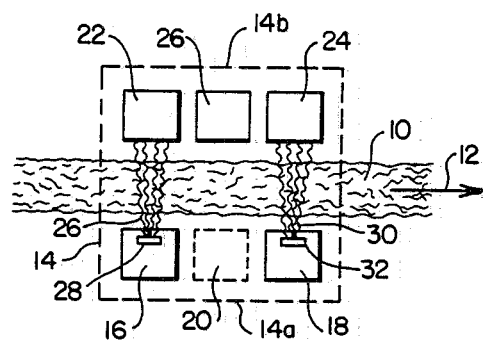
FIG. 1 is a schematic showing of an arrangment of sensing apparatus according to the invention.

Referring to FIG. 1, the numeral 10 indicates a glass fiber mat, traveling in the direction of the arrow 12. Typically the mat 10 has passed through curing ovens (not shown) and has just been cooled by a current of air that is passed over and through the mat by cooling fans (not shown). A more complete showing and description of a typical glass fiber mat manufacturing process is contained in the Sturm application No. 431,179 supra.

The area of the process shown in FIG. 1 is a measuring zone wherein there is located a gauge housing and bracket assembly designated by the dashed line 14. Assembly 14 includes a lower housing 14a containing two radiation source units 16 and 18 and a space for an infrared radiation detector unit 20. An upper housing 14b contains two radiation detector units 22 and 24 and an infrared radiation source or source and detector unit 26. The infrared radiation detector space 20 is indicated by dashed lines, since commonly the mass per unit area of the mat 10 is beyond the useful penetration range of infrared radiation. In such a case the infrared detector 20 may be omitted and the unit 26 may comprise an infrared radiation reflection source and detector combination unit whose only function is to enable a binder cure measurement.

The binder weight measurement according to this invention is enabled by the radiation gauges 16, 22 and 18, 24. The source unit 16 directs into the traveling mat 10 gamma rays 26 from a first radiation source 28 comprising americium-241 isotope. The detector unit 22 typically comprises an ionization chamber which is conventionally "tuned" for efficient detection in particular of the 60 kev gamma rays from the mat 10, i.e., the rays 26 from source 28 which have penetrated the mat.

Similarly the source unit 18 directs into the traveling mat 10 isotopic X-rays 30 from a second radiation source 32 comprising curium-244 isotope. The detector unit 24 typically comprises an ionization chamber which is conventionally tuned for efficient detection in particular of the isotopic X-rays in the range of about 14 to 21 kev from the mat 10, i.e., the rays 30 from source 32 which have penetrated the mat. The rays 30 per se are practically indistinguishable from gamma rays, but are properly termed X-rays because of the particular nuclear/atomic process that produces them as a result of the normal decay of the curium-244 isotope.

The radiation gauges 16, 22 and 18, 24 are installed in the housing and bracket assembly 14 with the infrared gauge 20, 26 in between so as to minimize as much as possible the number of gamma rays 26 that are scattered into the isotopic X-ray detector 24, and the number of isotopic X-rays 30 that are scattered into the gamma-ray detector 22. This minimizes undesirable cross talk between the two instruments.

Figure 2:
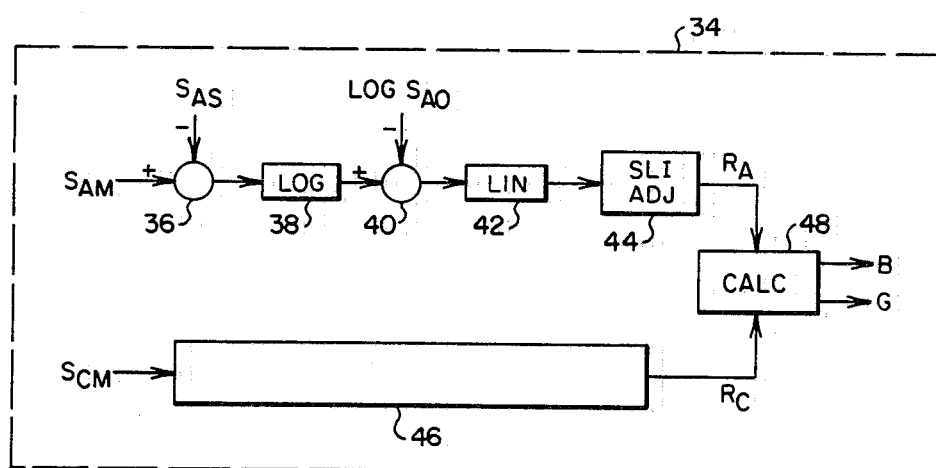
FIG. 2 is a schematic showing of a signal processing arrangement for use in combination with the arrangment of FIG. 1.

The signal produced by detector 22 is conventionally amplified to produce a signal $S_{AM}$ (FIG. 2) and the signal produced by detector 24 similarly produces a signal $S_{CM}$. FIG. 2 has a dashed line enclosure representing a computer 34 wherein the indicated mathematical operations can be carried out. Typically computer 34 is a conventional digital device that is interfaced with the circuits of detectors 22 and 24 through an analog to digital converter (not shown) which delivers the signals $S_{AM}$ and $S_{CM}$ in digital form.

In addition to the signal $S_{AM}$, the gamma ray detector 22 supplies two other signals $S_{AS}$ and $S_{AO}$ which are derived and stored during convenient or periodic standardizing intervals. $S_{AS}$ is the signal output from detector 22 when a shutter (not shown) is closed over the americium-241 source 28. $S_{AO}$ is the signal output from detector 22 when the shutter is open and when the housing assembly has been moved to an "off-mat" position where the radiation beams 26 and 30 can pass directly to the detectors 22 and 24 without attenuation by the mat 10.

The shutter closed signal $S_{AS}$ is subtracted from the measuring signal $S_{AM}$ in an operation 36. The logarithm of the difference is taken at 38. The logarithm of the off-mat signal $S_{AO}$ is subtracted at 40 from the logarithm derived at 38. The result, representing the logarithm of the ratio of the off-mat and measuring signals, is then linearized in operation 42 according to a function such as $$y = \frac{x}{a + bx + cx^2 + dx^3}$$

where x represents the result of operation 40, y represents the linearized value of the result, and a, b, c and d are constants determined in calibration. A slope and intercept adjustment is then performed on the linearized value, in operation 44.

Operation 44 comprises multiplying each linearized value by a slope constant and adding an intercept constant. The slope and intercept constants are selected to calibrate the resulting response values $R_A$ so that $R_A$ is adapted to correctly indicate the mass per unit area of a mat 10 of glass fibers having no resinous binder thereon. This calibration can be performed by conventional methods using specially prepared glass mat samples without binder, or synthetic calibration samples, or by extrapolation, to zero binder weight, of values derived with the use of actual samples of the mat 10 having binder weights that are known or which are laboratory determined.

In the same manner as just described, the signals $S_{CM}$ from the curium isotopic X-ray detector 24 are processed in a second channel 46 to produce a second response $R_C$, which like the first response RA is calibrated so that it is adapted to correctly indicate the mass per unit area of a mat of glass fibers having no resinous binder thereon.

That is to say, if the response values are fed to a suitable printer, decimal display unit or recorder, for example, the indicated values may be in accordance with $$R_A = G + mB \quad (1)$$

and $$R_C = G + nB \quad (2)$$

where G represents the mass per unit area of only the glass fibers in the mat 10, B represents the mass per unit area of only the binder, and m and n are termed relative binder weight sensitivity constants.

The computer 34 forms a combination of the first and second responses $R_A$ and $R_C$ by solving equations (1) and (2) in a calculation operation 48 to produce a third response B that is indicative of the mass of the binder per unit area of the mat 10 according to $$B = \frac{R_A - R_C}{m - n} \quad (3)$$

This response is substantially independent of the mass of the glass fibers.

A fourth response G may also be calculated in in operation 48, according to $$G = \frac{mR_C - nR_A}{m - n} \quad (4)$$

where G represents the mass of the glass fibers per se and is substantially independent of the mass of the binder.

While the invention has been shown and described as being embodied in certain specific procedures and apparatus, such showing and description are meant to be illustrative only and not restrictive, since many changes, modifications and outwardly different embodiments can obviously be made without departing from the spirit and scope of the invention.

What is claimed is:

1. The method of measuring a traveling mat of glass fibers that have been coated with a resinous binder, so as to determine quantitatively the mass of binder per unit area of the mat, the method comprising
   directing into the traveling mat gamma rays from a first radiation source comprising americium-241 isotope,
   also directing into the traveling mat isotopic X-rays from a second radiation source comprising curium-244 isotope,
   detecting the gamma rays from the traveling mat to produce a first response,
   detecting the isotopic X-rays from the traveling mat to produce a second response, and
   forming a combination of the first and second responses so as to produce a third response that is indicative of the mass of the binder and substantially independent of the mass of the glass fibers.

2. A method as in claim 1 which comprises calibrating the first and second responses so that both responses are adapted to correctly indicate the mass per unit area of a mat of glass fibers having no resinous binder thereon, the combination being formed from the calibrated responses.

3. A method as in claim 1 which comprises forming a second combination of the first and second responses so as to produce a fourth response that is indicative of the mass of the glass fibers and substantially independent of the mass of the binder.

4. A method as in claim 2 which comprises forming a second combination of the first and second responses so as to produce a fourth response that is indicative of the mass of the glass fibers and substantially independent of the mass of the binder.

5. Apparatus for measuring a traveling mat of glass fibers that have been coated with a resinous binder, so as to determine quantitatively the mass of binder per unit area of the mat, the apparatus comprising
   means for directing into the traveling mat gamma rays from a first radiation source comprising americium-241 isotope,
   means for directing into the traveling mat isotopic X-rays from a second radiation source comprising curium-244 isotope,
   means for detecting the gamma rays from the traveling mat to produce a first response,
   means for detecting the isotopic X-rays from the traveling mat to produce a second response, and
   means for forming a combination of the first and second responses so as to produce a third response that is indicative of the mass of the binder and substantially independent of the mass of the glass fibers.

6. Apparatus as in claim 5 which comprises means for calibrating the first and second responses so that both responses are adapted to correctly indicate the mass per unit area of a mat of glass fibers having no resinous binder thereon, and means for forming the combination from the calibrated responses.

7. Apparatus as in claim 5 which comprises means for forming a second combination of the first and second responses so as to produce a fourth response that is indicative of the mass of the glass fibers and substantially independent of the mass of the binder.

8. Apparatus as in claim 6 which comprises means for forming a second combination of the first and second responses so as to produce a fourth response that is indicative of the mass of the glass fibers and substantially independent of the mass of the binder.

* * * * *